United States Patent
Baird et al.

(10) Patent No.: US 10,632,082 B2
(45) Date of Patent: Apr. 28, 2020

(54) PROCESS FOR THE CONTINUOUS MANUFACTURE OF A POLYISOBUTYLENE BASED TRANSDERMAL PATCH

(75) Inventors: Russell Adam Baird, Atlanta, GA (US); Brad L. Barnett, Swanton, VT (US); Russell D. Beste, S. Burlington, VT (US)

(73) Assignee: Mylan Inc., Canonsburg, PA (US)

(*) Notice: Subject to any disclaimer, the term of this patent is extended or adjusted under 35 U.S.C. 154(b) by 0 days.

(21) Appl. No.: 12/838,919

(22) Filed: Jul. 19, 2010

(65) Prior Publication Data

US 2011/0020426 A1 Jan. 27, 2011

Related U.S. Application Data

(60) Provisional application No. 61/271,398, filed on Jul. 21, 2009.

(51) Int. Cl.
*A61K 9/70* (2006.01)
*C09J 123/22* (2006.01)
*C08L 23/22* (2006.01)

(52) U.S. Cl.
CPC ........... *A61K 9/7053* (2013.01); *C09J 123/22* (2013.01); *C08L 23/22* (2013.01); *C08L 2205/02* (2013.01); *C08L 2666/06* (2013.01)

(58) Field of Classification Search
USPC ........................................................ 424/449
See application file for complete search history.

(56) References Cited

U.S. PATENT DOCUMENTS

| | | | |
|---|---|---|---|
| 3,634,381 A * | 1/1972 | Lehnerer | B29C 47/38 425/202 |
| 4,285,655 A | 8/1981 | Matsubara | |
| 4,559,222 A | 12/1985 | Enscore et al. | |
| 5,079,008 A | 1/1992 | Sinnreich et al. | |
| 5,508,038 A | 4/1996 | Wang et al. | |
| 5,662,926 A | 9/1997 | Wick et al. | |
| 5,704,555 A * | 1/1998 | Arastoopour | B29B 13/10 241/16 |
| 6,365,178 B1 | 4/2002 | Venkateshwaran et al. | |
| 6,492,022 B2 * | 12/2002 | Tang et al. | 428/364 |
| 6,555,130 B2 | 4/2003 | Wustling et al. | |
| 2001/0039302 A1 | 11/2001 | Wustling et al. | |
| 2004/0009202 A1 | 1/2004 | Woller | |

FOREIGN PATENT DOCUMENTS

| | | |
|---|---|---|
| CN | 1732937 A | 2/2006 |
| JP | 01-311017 | 12/1989 |
| JP | 08-073694 | 3/1996 |
| JP | 2007528392 A | 10/2007 |
| KR | 960005143 B1 | 4/1996 |
| WO | 2005091852 A2 | 10/2005 |

OTHER PUBLICATIONS

Fox and Flory (J. Phys. Chem., 1949, 53 (2), pp. 197-212).*
BASF (BASF Oppanol product guide, http://www.dispersions-pigments.basf.com/portal/load/fid736992/Brochure_%20Oppanol%20-%20PIB%20by%20BASF.pdf, downloaded May 7, 2014).*
Heino and Seppala (Polymer Bulletin 30, 353-360 (1993 )).*
International Search Report and Written Opinion, PCT/US2010/042428, dated Oct. 15, 2010.
Canadian Office Action for Application No. 2,768,646 dated Feb. 19, 2013.
New Zealand Examination Report for Application No. 597993 dated Apr. 5, 2013.
Jun et al., "Hot Melt Adhesives Practical Handbook", Chemical Industry Press, May 2004, p. 66.
Australian Examination Report for Application No. 2010276456 dated Oct. 1, 2013.
Chinese Office Action for Application No. 201080042119.5 dated Dec. 17, 2013.
Chinese Office Action for Application No. 201080042119.5 dated May 20, 2013.
Chinese Office Action for Application No. 201080042119.5 dated May 23, 2014.
Japanese Office Action for Application No. 2012-521705 dated Oct. 18, 2013.
Russian Office Action for Application No. 2012106117 dated Apr. 7, 2014.
Indian First Examination Report for Appln. No. 845/DELNP/2012 dated Aug. 31, 2015.
Scaffaro, R. and Maio, A., Enhancing the mechanical performance of polymer based nanocomposites by plasma-modification of nanoparticles, Elsevier Ltd., Polymer Testing 31 (2012) 889-894.
English Language Abstract of JP 2007 528392 (J-PLAT PAT).
English Language Abstract of KR 960005143 (KIPRIS (Korea Intellectual Property Rights Information Service)).

* cited by examiner

*Primary Examiner* — Devang K Thakor (57) ABSTRACT

The present invention is directed to a process for manufacturing a transdermal delivery device comprising a backing layer, a release liner, and an adhesive layer between the backing layer and release liner. More specifically, the invention is directed to a process of preparing an adhesive layer, wherein the adhesive layer is comprised of polyisobutylene and an active pharmaceutical ingredient.

15 Claims, 3 Drawing Sheets

PROCESS FOR THE CONTINUOUS MANUFACTURE OF A POLYISOBUTYLENE BASED TRANSDERMAL PATCH

CROSS-REFERENCE TO RELATED APPLICATIONS

This application claims the benefit of the filing date of U.S. Provisional Patent Application No. 61/271,398 filed Jul. 21, 2009, the disclosure of which is hereby incorporated herein by reference.

BACKGROUND OF THE INVENTION

This invention relates to methods of preparing pressure sensitive adhesive matrix layers for transdermal drug delivery.

The delivery of drugs through the skin provides many advantages. Primarily, it is a comfortable, convenient and non-invasive way of administering drugs. Moreover, such a means of delivery provides for uninterrupted therapy and a higher degree of control over drug concentrations in the blood.

Transdermal delivery of various active pharmaceutical ingredients ("API") and pressure sensitive adhesive matrix patches for transdermal delivery of such APIs are well known in the art of drug delivery. These matrix patches include a pressure sensitive adhesive layer for affixing the patch to the skin and for carrying the API and any excipients that are directly incorporated into this adhesive layer into the body. These adhesive matrix patches also typically include an inert backing layer to provide support, and a release liner which covers and protects the adhesive. The release liner is peeled off and discarded before applying the patch to the skin. These patches are distinguished from reservoir patches in that the API in a reservoir patch is incorporated in a layer or compartment, with a differing material composition, separate from the pressure sensitive adhesive layer. One type of adhesive commonly used in the adhesive layer is polyisobutylene ("PIB").

When such adhesives are used in transdermal delivery devices it is necessary that they exhibit a reasonable permeability to the API being delivered and, when they are used in combination with a rate-controlling membrane, the adhesive layer preferably exhibits a higher permeability to the API than the rate controlling membrane.

Mixtures of high and low molecular weight PIBs are known in the art as adhesives, however they are relatively impermeable to many APIs. As a result, the prior art PIB adhesives usually contain a plasticizer such as mineral oil ("MO") or polybutene to achieve sufficient permeability to permit API migration through the adhesive at rates which are therapeutically useful from reasonably sized systems.

For example, U.S. Pat. No. 4,559,222 is directed to compositions comprising PIB in conjunction with copious amounts of mineral oil to deliver the active agent clonidine. In particular, the systems described use a ratio of mineral oil to PIB of at least 1.0, and preferably higher amounts, in the API delivery matrix. Here, the mineral oil acts to plasticize the adhesive and to increase the permeability of the adhesive composition to the API.

U.S. Pat. No. 5,508,038 is directed to an adhesive which is useful as an adhesive in transdermal delivery devices. The adhesive comprises mixtures of high molecular weight ("HMW") and low molecular weight ("LMW") PIBs in weight ratios of about 5-40 HMW PIB: 95-60 LMW PIB which are substantially free of plasticizers and tackifiers. The system is processed by solvent coating the mixture of PIBs and API onto a release liner and then evaporating the solvent from the API/PIB adhesive matrix. The process is limited to a batch of solvated PIB and API, as well as limited by the necessity and cost of evaporating solvent from the adhesive matrix. Moreover, in the case of highly volatile APIs, it is difficult to evaporate the solvent without also evaporating at least part of the API.

U.S. Pat. No. 6,365,178 is directed to a method of making a pressure sensitive matrix patch for transdermal delivery of an API. The method includes the steps of dissolving a hydrophilic salt form of an API in a water phase of an aqueous dispersion of a hydrophobic pressure sensitive adhesive, casting the resulting mixture as a thin film, and evaporating the water. Similar to U.S. Pat. No. 5,508,038 described above, PIB in a solvent is used to coat a release liner.

U.S. Pat. No. 6,555,130 describes the use of a twin screw extruder to make a continuous film of adhesive/API. The patent, however, discloses only the use of granulated PIB which necessitates a filler or coating material, such as talc, to prevent agglomeration of the granulated PIB. Not only does the granulation step and incorporation of filler materials add costly processing steps, it also complicates the final formulation and could negatively impact chemical stability or physical properties.

The art described thus far involves either solvent coating the FIB and API or the use of excipients, such as mineral oil, to vary the rate of API release. It is desirable, however, to substantially eliminate the use of solvents or the use of such excipients.

The advantage of foregoing the use of solvents lies essentially in the simplification of the coating process. The avoidance of flammable solvents does away with the need for drier units, with their high energy consumption, for the evaporation and recovery of the solvents, and with the need to use explosion-protected units. Hot-melt coating units are compact and permit much higher coating speeds. The technology is environmentally-friendly, with no solvent emissions. Furthermore, no unwanted solvent residues remain in the self-adhesive composition.

BRIEF SUMMARY OF THE INVENTION

In accordance with the present invention, Applicants have discovered a solvent-free process of preparing an adhesive layer or adhesive composition, wherein the adhesive layer is comprised of PIB and an API. The adhesive layer or adhesive composition formed in accordance with the current invention can be incorporated into a transdermal delivery device or patch.

In accordance with one embodiment of the present invention, HMW PIB is fed into an extruding apparatus where it is mixed with LMW PIB; an API is then added to the mixture of PIBs to produce an API/PIB melt; the API/PIB melt is then discharged to a die to form a thin adhesive sheet. In preferred embodiments, no additional solvents are added and, thus the process is considered "solvent free" as that term is defined herein. The process does not require granulation with fillers or plasticizers, but these components may be present in the starting materials in acceptable amounts. For example, fillers or plasticizers may be present in amounts of about 5% by weight of each starting material.

In accordance with another embodiment of the present invention, the HMW PIB is pre-processed in a single screw extruder before being fed into a second extruding apparatus. In accordance with another embodiment of the present invention, the single screw extruder is heated to a temperature between about the glass transition temperature of the HMW PIB and about 500° F., so as to heat the HMW PIB. In accordance with another embodiment of the present invention, the single screw extruder is heated to a temperature between about 150° F. and about 350° F.

In accordance with another embodiment of the present invention, HMW PIB has a number average molecular weight ($M_n$) ranging from about 100,000 g/mol to about 800,000 g/mol. In accordance with another embodiment of the present invention, the HMW PIB has a number average molecular weight ($M_n$) ranging from about 200,000 g/mol to about 425,000 g/mol. In accordance with another embodiment of the present invention, the HMW PIB is free from fillers. In accordance with another embodiment of the present invention, the HMW PIB is free of talc.

In accordance with another embodiment of the present invention, the extruder used to mix the HMW PIB and the LMW PIB is a twin screw extruder. In accordance with another embodiment of the present invention, the twin screw extruder utilizes co-rotating screws.

In accordance with another embodiment of the present invention, the LMW PIB has a molecular weight ranging from about 35,000 g/mol to about 100,000 g/mol. In accordance with another embodiment of the present invention, the LMW PIB has a molecular weight ranging from about 36,000 g/mol to about 75,000 g/mol.

In accordance with another embodiment of the present invention, the LMW PIB is heated to a temperature between about room temperature and about 500° F. before mixing with the HMW PIB. In accordance with another embodiment of the present invention, the LMW PIB is heated to a temperature between about 150° F. and about 350° F. before mixing with the HMW PIB.

In accordance with another embodiment of the present invention, a ratio of the HMW PIB to the LMW PIE in the PIB melt ranges from about 20:80 to about 85:15.

In accordance with another embodiment of the present invention, the API is selected from the group consisting of lidocaine, testosterone, tulobuterol, buprenorphine, dextroamphetamine, flurbiprofen, rotigotine, risperidone, dexketoprofen, ketoprofen, hydrocortisone, cortisone, dexamethasone, prednisolone, prednisone, halcinonide, methylprednisolone, flurocortsone, corticosterone, paramethasone, fentanyl, sufentanil, ibuprofen, naproxen, fenoprofen, fenbufen, indoprofen, salicylic acid, methylslicyate, sulindac, mefenamic acid, piroxicam, indonisilone, tolmetin, propranolol, isosorbide dinitrate, isosorbide mononitrates, diltiazem, nifedipine, procinamide, methyltestosterone, fluoxmesterone, 1-B estradiol valerate, equilin, mestranol estrone, estriol, diethylstilbestrol, progesterone, 19-norprogesterone, norethindrone, melengetrol chloradinone, ethisterone, medroxyprogesterone acetate, hydroxyprogesterone caproate, noethynodrel, dimethisterone, ethinylestrenol, norgestrel, megestrolacetate, ethinodiol diacetate, chloral hydrate, benzdiazepines, naloxone, haloperidol, pentobarbitol, phenobarbitol, secobarbitol, codeine, dibucaine, benzocaine, fentanyl analogs, diphenhydramine, triprolidine, chlorcyclizine, promethazine, cyclizine, chlorprenaline, terrenadine, phenylpropanolamine, chlorpheniramine, pilocarpine, atropine, methantheline, papverine, cinnmedrine, methscopolamine, naltrexone, isocaboxazide, phenelzine, imipramine, amitrptyline, trimepramine, dozepin, desipramine, nortriptyline, protriptyline, amoxapine, maprotiline, tamoxifen, tetracycline, chloramphenicol, sulfacetamide, sulfadiazine, sulfamerazine, sulfoxazole, idoxuridine, erythromycin, antazoline, metapyriene, pyrilamine, aspirin, salicylamide, dihdroergotamine, pizotyline, reserpine, chlorpromazine, antianxiety benzodiazepines, helperidol loxapine, molindone, thiothixene, pimozide, quetiapine fumarate, olanzapine, and phenothiazine derivatives.

In accordance with another embodiment of the present invention, an amount of API in the adhesive composition ranges from about 0.01% to about 40% by weight of the API/PIB melt. In accordance with another embodiment of the present invention, the method further comprises adding one or more additives to the API/PIB melt.

In accordance with another embodiment of the present invention, the invention further comprises laminating the formed adhesive thin sheet between a backing layer and a release liner to produce a transdermal delivery device. In some embodiments, the transdermal delivery device is monolithic. In accordance with another embodiment of the present invention, the transdermal delivery device may further comprise a membrane layer and a skin-contact layer.

In accordance with the present invention, Applicants have discovered an adhesive composition comprising an API and PIB, wherein the composition is substantially free from fillers and produced according to the methods described herein. In one embodiment, the API is lidocaine. In another embodiment, the API is piroxicam. In another embodiment, the API is fentanyl. In another embodiment, the API is sufentanil. In another embodiment, the adhesive composition is incorporated into a transdermal delivery device.

Applicants have surprisingly found that it is possible to continuously create a solvent-free adhesive layer for incorporation in a transdermal delivery device without the need to granulate the adhesive and/or API with fillers or other materials. Moreover, Applicants have found that such a process is well suited for thermally labile and highly volatile APIs because no evaporation step is required.

DETAILED DESCRIPTION

In general, the present invention is directed to a solvent-free process for manufacturing a transdermal delivery device or patch comprising a backing layer, a release liner, and an adhesive layer between the backing layer and release liner.

More specifically, the invention is directed to a solvent-free process of preparing an adhesive layer, wherein the adhesive layer is comprised of polyisobutylene and an active pharmaceutical ingredient.

As used herein, the term "active pharmaceutical ingredient" or "API" is used to describe the principal active ingredient of the transdermal delivery device, which is a biologically active compound or mixture of compounds that has a therapeutic, prophylactic and/or physiological effect on the wearer of the device.

As used herein, the term "solvent free" means that the manufacturing process does not use solvents, or uses solvents (either added or present in the starting materials) in an amount of less than about 85% of the quantities normally used in the manufacture of a transdermal delivery device or patch.

As used herein, "transdermal" means delivery of an API by passage into and through the skin or mucosal tissue.

Figure 1:
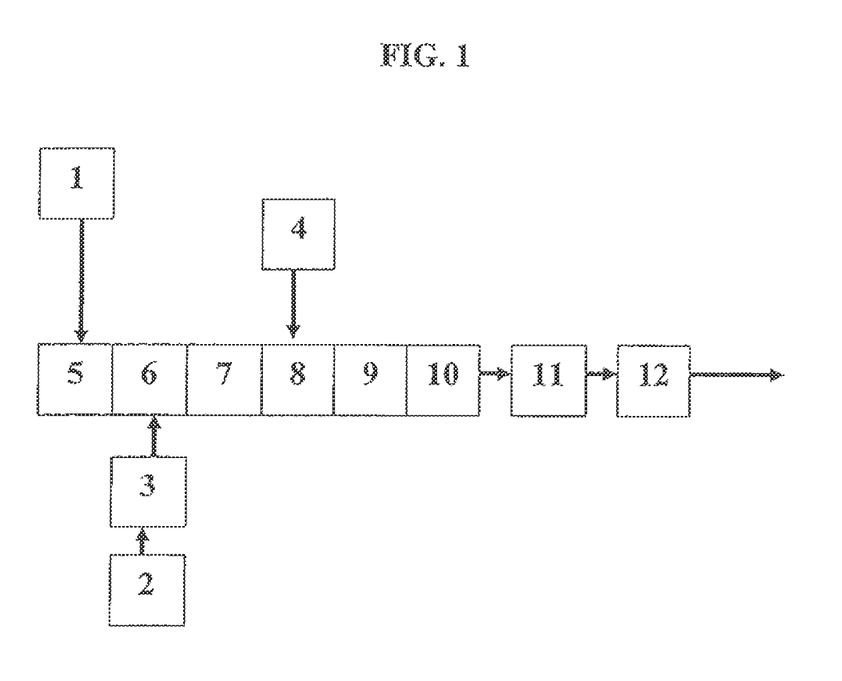
FIG. 1 is a schematic overview of a process for manufacturing a polyisobutylene based transdermal delivery device.

With reference to the accompanying Figures, HMW PIB is fed in bulk form into an extruder, preferably a single screw extruder 1 where an auger blade rotates and compresses the bulk HMW PIB material into a continuous feed for further processing. In some embodiments, the HMW PIB material leaving the single screw extruder 1 is, generally, in the form of a continuous block or cylinder of material. Of course, at this stage, the material may have any form, including a rope-like shape. It is believed that this allows for a constant metered supply of HMW PIB material to be passed to a metering zone of a twin screw extruder 5. Of course, the form of the material can be in any shape or size provided it does not interfere with or hinder subsequent processing.

Any single screw extruder 1 may be used provided that it can appropriately process HMW PIB in accordance with the objectives of the present invention. For example, the single screw must be able to provide a consistent output for further processing, i.e. there must be consistency in the size, shape, and quantity of material being mixed and subsequently output. Accordingly, any size screw may be used provided it provides sufficient throughput of material without overpowering any further downstream processes. By way of example only, a two inch screw can be used to provide about a 10 kg/hr throughput for thin film formation. In this example, it is believed that such a throughput would not overload downstream processes, including a comparably rated twin screw extruder.

Examples of suitable single screw or single feed extruders include those available from The Bonnot Company (1520 Corporate Woods Parkway, Uniontown, Ohio 44685), Diamond America, Coperion, Troester/ESI, and Davis-Standard.

In some embodiments, the auger, or the single screw extruder in general, utilizes a temperature ranging between the HMW PIB glass transition temperature (about −85° F.) and about 500° F. In other embodiments, the auger or the single screw extruder is heated to a temperature ranging between about 150° F. and about 350° F. In yet other embodiments, the auger or the single screw extruder is heated to a temperature between about 200° F. and about 300° F. Of course, any temperature or pressure can be applied such that the extruder remains full of material and provides consistent output.

Any molecular weight HMW PIB may be used provided that the molecular weight does not interfere with the process or resulting transdermal delivery device, e.g. does not interfere with the machinery including the auger and/or mechanics of the extruder, does not have difficulty shearing or compressing, does not become degraded by high temperatures, or does not cold flow, etc. Typically, HMW PIB having a weight ranging between about 800,000 g/mol and above about 100,000 g/mol is used. In some embodiments, the HMW range is between about 200,000 g/mol and 425,000 g/mol. In other embodiments, the HMW PIB has a number average molecular weight of about 250,000 g/mol. It is believed that HMW PIB above about 800,000 g/mol will not be able to be processed properly, i.e. the material is believed to undergo shear degradation in the extruder(s). Moreover, it is believed that at molecular weights at or below 100,000 g/mol, the HMW PIB will cold flow and deform. Thus, a molecular weight should be chosen such that the finished system a) will not cold flow or only minimally cold flow, and b) provides for a soft enough adhesive such that the resulting patch is flexible and easy-wearing.

"Cold flow" of an adhesive is understood to be the continuing dimensional change, usually caused by gravity's effect on the adhesive matrix on the outer boundaries of the system prior to use, at ambient storage conditions. This is particularly disadvantageous for adhesive layers which contain API in transdermal therapy systems, because the absorption of the active substance by the body is influenced in an uncontrollable manner. It also causes difficulty removing the system from the storage pouch and is unsightly.

Those skilled in the art will appreciate that the PIBs can be mixed with any suitable modifier, such as talc, fumed silica, calcium carbonate, bentonite, barium sulfate, wax, clay, carbon black, and starch.

HMW PIB is available from several manufacturers including BASF where it is sold under the trade name Oppanol® (BASF Corporation, 100 Campus Drive, Florham Park, N.J. 07932 USA). Other manufacturers include Exxon and Rit-Chem.

The material from 1 is then further processed into smaller domains in a metering zone of a twin screw extruder 5. This is accomplished by further shearing the HMW PIB material and then metering it on the twin screw extruder.

Any twin screw extruder may be used provided that it can appropriately process the PIB and API in accordance with the objectives of the present invention. For example, the twin screw extruder must be able to adequately mix the PIBs and API and must be able to provide a consistent output for further processing. Suitable twin screw extruders should also have one or more metering zones where additional ingredients (e.g. PIB, API, or additives) could be introduced. In some embodiments, the extruder has between 1 and 10 metering zones. Examples of suitable twin screw extruders include those available from American Leistritz (169 Meister Ave., Somerville, N.J. 08876-3464), Prism, Farrel, Coperion, Berstorff, and Buhler. In some embodiments, the twin screw extruder contains counter-rotating screws. In other embodiments, the twin screw extruder contains co-rotating screws. In some embodiments, co-rotating screws are believed to provide a more consistent mixture and feed of material than counter-rotating screws.

The material being processed in the twin screw extruder may optionally be kept in an inert atmosphere, e.g. an atmosphere comprising nitrogen and/or argon. The use of an inert atmosphere may be needed when, for example, the API selected is unstable in an environment containing oxygen or when high temperatures are used.

The twin screw extruder should have one or, preferably, a plurality of separate temperature control or cooling circuits in order to permit a temperature regime which allows the use of thermally sensitive PIBs or active pharmaceutical ingredients. In cases where this is unnecessary, the temperature control circuits may also be combined with one another in order to minimize the number of temperature control devices.

The HMW PIB material from 5 is then mixed with low molecular weight PIB ("LMW PIB") in a separate metering zone 6 of the twin screw extruder. The LMW PIB is added via an inlet on the twin screw extruder, such as a standard liquid injection port.

The LMW PIB must first be prepared before it is injected into the twin screw extruder. The LMW PIB, which has a consistency of cold syrup at room temperature (for example, a temperature between about 65° F. and about 75° F. and a viscosity range of about $10^6$ to about $10^8$ centipoise), is heated by a plenum-type drum unloader to a temperature ranging between about room temperature (65-75° F.) to about 500° F., preferably between about 150° F. to about 350° F.

The pump on the drum unloader provides a constant pressure behind the LMW PIB which facilitates transfer to a gear pump 3. Typically, a pressure between about 30 psi and about 150 psi is applied, preferably between about 65 psi and about 100 psi.

The gear pump 3 is used to consistently meter the LMW PIB to the inlet in the twin screw extruder 6 where it is mixed with the HMW PIB. The gear pump is also heated to a temperature between about room temperature, i.e. about 65° F. to about 75° F., and about 500° F., preferably between about 200° F. and about 300° F.

Any molecular weight LMW PIB may be used provided that the weight does not interfere with the process, e.g. does not interfere with the twin screw extruder or any of its components, does not have difficulties being sheared or compressed, does not become degraded by high temperatures, etc. Typically, LMW PIB having a weight ranging between about 100,000 g/mol and about 35,000 g/mol is used. In some embodiments, LMW having a weight ranging between about 75,000 g/mol and about 36,000 g/mol is used. In other embodiments, the LMW PIB has a number average molecular weight of about 51,000 g/mol. Without wishing to be bound by any particular theory, it is believed that LMW PIB at or above about 100,000 g/mol will be unable to impart sufficient tack to the adhesive matrix to properly adhere to the skin. Moreover, it is believed that at molecular weights below 35,000 g/mol, the LMW PIB will cold flow and deform, as defined herein.

LMW PIB is available from several manufacturer's including BASF, under the trade name Oppanol®. Other manufacturers include Exxon and Rit-Chem.

Any ratio of HMW PIB to LMW PIB may be used provided that: (a) the resulting transdermal delivery device is not too stiff to adhere properly to the skin of the patient (which, it is believed, can be the result of too much HMW PIB); (b) the resulting device is difficult to remove from the skin (which, it is believed, can be the result of too much LMW PIB); or (c) the adhesive layer cold flows (which, it is believed, can be the result of too much LMW PIB).

In some embodiments, the ratio of HMW PIB to LMW PIB in the PIB mixture, or final device, ranges from about 20:80 to about 85:15. In other embodiments, the ratio of HMW PIB to LMW PIB ranges from about 35:65 to about 85:15. In yet other embodiments, the ratio of HMW PIB to LMW PIB ranges from about 50:50 to about 70:30. In yet further embodiments, the ratio of HMW PIB to LMW PIB is about 65:35. The ratio of HMW PIB to LMW PIB depends, of course, on the type and amount API used and the desired rate of API delivery.

The total amount of PIB (i.e., the amounts of HMW PIB and LMW PIB combined) in the adhesive layer ranges from about 60% to about 99.99% by weight of the adhesive layer, preferably ranging from about 85% to about 99% by weight of the adhesive layer, more preferably ranging from about 93% to about 97% by weight of the adhesive layer. Again, this varies according to the type and amount of API used.

The mixture of HMW PIB and LMW PIB is then passed to a high shear mixing zone 7 of the twin screw extruder which is used to create a melt. The melt seal allows for induction of the API in the PIB adhesive.

The API may be any therapeutic agent capable of being included within a transdermal delivery device. Non-limiting examples of active pharmaceutical ingredients include anti-inflammatory substances, opioid receptor antagonists, opiates, μ-opioid agonists, anticholinergics, coronary dilators, cerebal dilators, peripheral vasodilators, alpha-adrenergic blockers, anti-infectives, psychotropics, anti-manics, stimulants, anti-histamines, decongestants, gastro-intestinal sedatives, anti-anginal drugs, vasodilators, anti-arrhythmics, anti-hypertensive drugs, vasoconstrictors, migraine treatments, anti-coagulants and anti-thrombotic drugs, analgesics, anesthetics, local anesthetics, anti-pyretics, hypnotics, sedatives, anti-emetics, anti-nauseants, anti-convulsants, neuromuscular drugs, hyper- and hypoglycemic agents, thyroid and anti-thyroid preparations, diuretics, anti-spasmodics, anti-emetic, uterine relaxants, anti-obesity drugs, anabolic drugs, erythropoietic drugs, sedatives, anti-asthmatics, bronchodilators, expectorants, mucolytics, anti-uricemic drugs, contraceptives, and the like.

In some embodiments of the present invention, the active pharmaceutical ingredient is selected from compounds including testosterone, tulobuterol, buprenorphine, dextroamphetamine, flurbiprofen, rotigotine, respiridone, dexketoprofen, ketoprofen, diclofenac, rivastigmine, granisetron, nicotine, methylphenidate, lidocaine, tetracaine, prilocalne and bupivicaine, hydrocortisone, cortisone, dexamethasone, prednisolone, prednisone, halcinonide, methylprednisolone, flurocortsone, corticosterone, paramethasone, ibuprofen, napoxen fenoprofen, fenbufen, indoprofen, salicylic acid, methylslicyate, sulindac, mefenamic acid, piroxicam, indonisilone, tolmetin, propranolol, isosorbide dinitrate, isosorbide mononitrates, diltiazem, nifedipine, procinamide, methyltestosterone, fluoxmesterone, 1-B estradiol valerate, equilin, mestranol estrone, estriol, diethylstilbestrol, progesterone, 19-norprogesterone, norethindrone, melengetrol chloradinone, ethisterone, medroxyprogesterone acetate, hydroxyprogesterone caproate, noethynodrel, dimethisterone, ethinylestrenol, norgestrel, megestrolacetate, ethinodiol diacetate, chloral hydrate, benzdiazepines, naloxone, haloperidol, pentobarbitol, phenobarbitol, secobarbitol, codeine, dibucaine, benzocaine, fentanyl analogs, diphenhydramine, triprolidine, chlorcyclizine, promethazine, cyclizine, chlorprenaline, terrenadine, phenylpropanolamine, chlorpheniramine, pilocarpine, atropine, methantheline, papverine, cinnmedrine, methscopolamine, naltrexone, isocaboxazide, phenelzine, imipramine, amitrptyline, trimepramine, dozepin, desipramine, nortriptyline, protriptyline, amoxapine, maprotiline, tamoxifen, tetracycline, chloramphenicol, sulfacetamide, sulfadiazine, sulfamerazine, sulfoxazole, idoxuridine, erythromycin, antazoline, metapyriene, pyrilamine, aspirin, salicylamide, dihdroergotamine, pizotyline, reserpine, chlorpromazine, antianxiety benzodiazepines, helperidol loxapine, molindone, thiothixene, pimozide, quetiapine fumarate, olanzapine, loratadine, desloratadine, dexmethylphenidate, and phenothiazine derivatives. In yet other embodiments, the active pharmaceutical ingredient is selected from compounds, including fentanyl, scopolamine, nitroglycerin, clonidine, 17-β estradiol, ethinyl estradiol, norelgestromin (and other hormones for birth control), selegiline, methylphenidate, oxybutynin, nicotine, diclophenac, or rivastigamine. Of course, any of these active pharmaceutical ingredients may be in the form of a salt, solvate, or hydrate or mixtures thereof. Also contemplated are derivatives or analogs of these compounds. In some embodiments, two or more APIs (in any form) may be combined.

In other embodiments of the present invention, the active pharmaceutical ingredient is lidocaine. As used herein, the term "lidocaine" is used to designate lidocaine, the salts, solvates, and hydrates of lidocaine or mixture thereof, and the related compounds thereof. In yet other embodiments, the active pharmaceutical ingredient is selected from piroxicam, fentanyl, and sufentanil (sufentanyl), or the salts, solvates, hydrates, or mixtures thereof.

The API can be dissolved within the HMW/LMW PIB mixture; partially dissolved and partially undissolved and dispersed within the PIB mixture; dispersed in a crystalline form in the PIB mixture; dispersed in an amorphous form in the PIB mixture; may be in an amorphous form partially dissolved and partially undissolved but dispersed in the PIB mixture; or may be a mixture of any one or more of these forms (e.g., a mixture of amorphous and crystalline. Without wishing to be bound by any particular theory, it is believed that crystallization is initiated more rapidly and uniformly when using the extrusion process of the present invention, as compared to traditional solvent cast methods.

The solubility, of course, depends on the particular system being employed, i.e. the solubility of the API in the adhesive matrix. In general, however, the solubility of the API in the adhesive layer ranges from about 0.1% to about 20% by weight at room temperature. In some embodiments, the system contains more drug than the solubility limit. In one particular example, the solubility of a lidocaine in a mixture HMW and LMW PIB ranges from about 0.1% to about 10% by weight at room temperature, preferably between about 2% to about 4% by weight at room temperature.

The amount of API in the adhesive layer ranges from about 0.01% to about 40% by weight of the adhesive layer, preferably ranging from about 0.1% to about 15% by weight of the adhesive layer, more preferably ranging from about 3% to about 7% by weight of the adhesive layer. Of course, the amount of API included depends on the potency of the API, its weight, and solubility in the PIB.

A feeder, preferably a side feeder, meters the API from a gravimetric feeder 4 into the twin screw extruder 8. In some embodiments, the temperature of the side feeder is maintained at a temperature below the melting point of the API. In some embodiments where the twin screw extruder is heated, it is necessary to cool the side feeder because the heat from the extruder could potentially pass through to the side feeder due to metal-to-metal contact. The API may be introduced into the extrusion apparatus at any stage and those skilled in the art will recognize that this may depend on API solubility, mobility, volatility, melting point, and degradation temperature. Also, the type of drug feed mechanism may be dictated based on the form of the API, e.g., ranging from liquid to coarse powder.

The API may be mixed with one or more additives including pH modifiers, binders, fillers, shear builders, diluents, absorbents, colorants, dyes, pigments, disintegrants, dispersants, flow aids, permeation enhancers, plasticizers, stabilizers, antioxidants, oxygen scavengers, dessicants, and anti-tacking agents. Examples of each of these are well known to those of ordinary skill in the art. Preferably, the additives are mixed with the API in the side feeder and before introduction into the twin screw extruder. Any amount of additive may be used, however, in general, the additive may account for up to 70% by weight of the adhesive layer.

In some embodiments, open flights are used at this zone of the extruder 8 to allow for easy API induction. The zone of the extruder where the API is introduced may optionally be heated, so as to melt the API. Generally, this temperature is between about 175° F. and about 250° F., but ultimately will depend on the API's properties, such as those detailed above.

The API and PIBs are then mixed 9, preferably with a variety of high shear mixing elements, to create a homogeneous mixture of the API and PIBs ("API/PIB melt").

The API/PIB melt is then pressurized 10 to provide a steady stream of material for subsequent downstream processing. Generally, the pressure applied on the extruder side is less than about 1500 psi, preferably between about 200 psi and about 500 psi. The actual pressure applied is a function of the percentage of API and also of the ratio of HMW PIB to LMW PIB as well as their respective molecular weights.

In communication with an end of the twin screw extruder is a gear pump 11. The gear pump 11 is used to mitigate variations in the upstream feed, and thus used to provide a consistent output of material for further processing. Generally, the gear pump may be heated to a temperature of above about the API melting temperature, but preferably within about +/−50° F. of the API melting temperature. Of course, one skilled in the art will avoid temperatures which could lead to the degradation of the API or excessive volatile loss of API. The pressure generated by the gear pump is a function of die temperature and the HMW PIB to LMW PIB ratio. As the amount of HMW PIB increases, the higher the effective pressure increases. Similarly, as the temperature of the gear pump decreases, the effective pressure increases.

After the API/PIB melt leaves the extruder, a die, e.g., a "coat-hanger" die 12, is used to shape the melt (such as from a "tube-like" cross-section to a more traditional flat sheet). The performance of the coat-hanger die is characterized by the flow uniformity at its outlet. The design of the die, in terms of slot thickness, die width, manifold profile and angle, can be optimized for acceptable performance over a range of melt properties. Any suitable die may be used including those described in U.S. Pat. No. 4,285,655, incorporated herein by reference.

Figure 2:
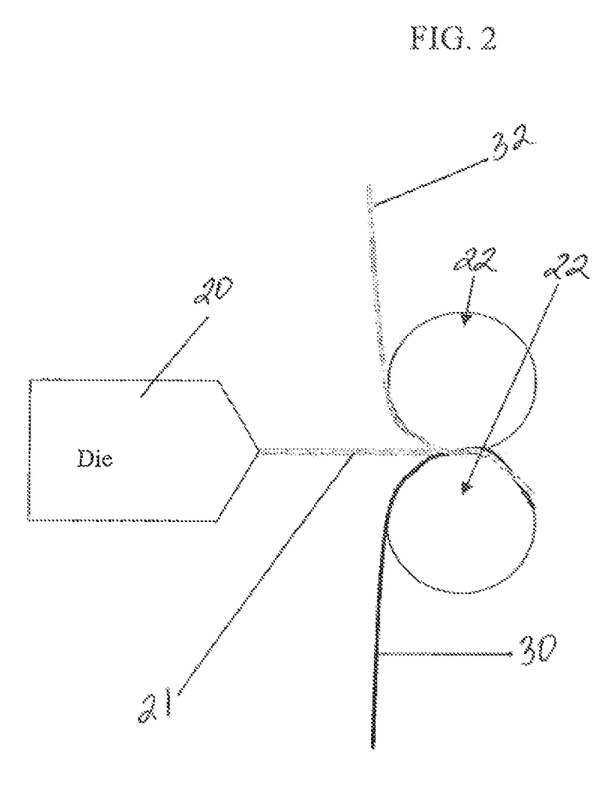
FIG. 2 is a schematic overview of a process of layering a material according to the present invention onto a backing material.
Figure 3:
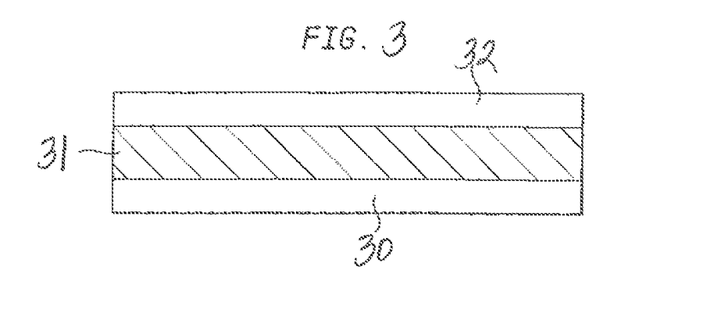
FIG. 3 is a schematic of a 3-layer transdermal delivery device made in accordance with the present invention.

After metering into the die 20, the flat sheet 21 is layered between a backing layer 30 and a release liner 32 by way of a roller, preferably a chilled roller 22, which is at a temperature between about 30° F. and about 100° F. A release liner 32 is adhered to the adhesive layer 31, opposite the backing layer 30. The use of a chilled roller is preferred so as to stop or prevent any degradation of the PIB and/or API.

The backing layer 30 is a flexible substrate which provides support for the adhesive during storage, handling and wear. Any well-known backing layer which satisfies this purpose can be used in the present invention.

Examples of materials from which the backing layer may be composed include polyethylene terephthalate, various nylons, polypropylenes, polyesters, polyester/ethylene-vinyl acetates, metalized polyester films, polyvinylidene chloride, metal films such as aluminum foils, polyvinylidene fluoride films, or mixtures or copolymers thereof.

Other non-limiting materials for the backing layer include ethylene vinyl acetate films laminated to a polyester, ethylene vinyl acetate films laminated to a metalized polyester, Mediflex® 1200 available from Mylan Technologies Inc., Mediflex® 1501 from Mylan Technologies Inc., Mediflex® 1505 from Mylan Technologies Inc., Mediflex® 1201 available from Mylan Technologies Inc., Mediflex® 1502 available from Mylan Technologies Inc., Dupont polyester type S available from Dupont, Dow BLF® 2050 available from The Dow Chemical Company, 3M™ Scotchpak® 1109 available from 3M, 3M™ Scotchpak® 9723 available from 3M, 3M™ Scotchpak® 9733 available from 3M, 3M™ Scotchpak® 9735 available from 3M and 3M™ Scotchpak® 9730 available from 3M.

Yet other suitable materials for the backing layer include polyethelene or polyolefin backings, such as Mediflex® 1000, 3M™ Cotran® 9722, and 3M™ Cotran™ 9720.

In preferred embodiments, the backing layer is comprised of ethylene vinyl acetate films laminated to a polyester, such as Mediflex® 1501 from Mylan Technologies, Inc.

In some embodiments, the backing layer may be the same size as the adhesive layer. In other embodiments, the backing layer may be oversized as compared with the adhesive layer, i.e. the backing layer may be larger than the adhesive layer. In yet other embodiments, the backing layer may range from about 0.01 mm to at least 10 mm larger than the adhesive matrix layer, preferably ranging from about 0.05 mm to about 5 mm larger than the adhesive matrix layer, and most preferably ranging from about 0.1 mm to about 3 mm larger than the adhesive matrix layer. Without wishing to be bound by any particular theory, it is believed that the use of an oversized backing layer helps prevent the adhesive matrix from becoming distorted or relaxing during the handling and/or shipping processes.

Release liners well known in the art can be used in the present invention. Non-limiting examples of materials from which the release liner may be composed include polyethylene terephthalate/silicone (i.e. polydimethyl siloxane) ("PET/SI"), polyethylene terephthalate/aluminized polyester coated with silicone (i.e. polydimethyl siloxane) ("PET/MET/SI"), polyester or polyurethane liners with a silicone coating, polyester or polyurethane liners with a fluorocarbon or fluorosilicone coating, or polyester or polyurethane liners with a silicon coating.

Specific release liners include Medirelease® 2249, Medirelease® 2226, Medirelease® 2500, 3M™ Scotchpak® 1020, 3M™ Scotchpack® 1022, 3M™ Scotchpak® 9741, 3M™ Scotchpak® 9742, 3M™ Scotchpak® 9744, CPFilms Inc. Clearsil® UV5A and CPFilms Inc., Clearsil® UV510, CPFilms Inc. Sil® UV5A and CPFilms Inc. Sil® UV510.

In some embodiments, the release liner may be the same size as the adhesive matrix layer and/or may be the same size as the backing layer. In other embodiments, the release liner may be larger than the adhesive matrix layer and/or may be larger than the backing layer. In yet other embodiments, the release liner may range from about 0.1 mm to at least about 20 mm larger than the margin of a backing layer or an adhesive matrix layer, preferably ranging from about 0.5 mm to about 10 mm larger than the backing layer or adhesive matrix layer, and most preferably ranging from about 1 mm to about 5 mm larger than the backing layer or adhesive matrix layer. It is believed that the use of an oversized release liner facilitates its removal by the user prior to application to the skin and may also help prevent the adhesive matrix from becoming distorted or relaxing during the handling and shipping processes.

Figure 4:
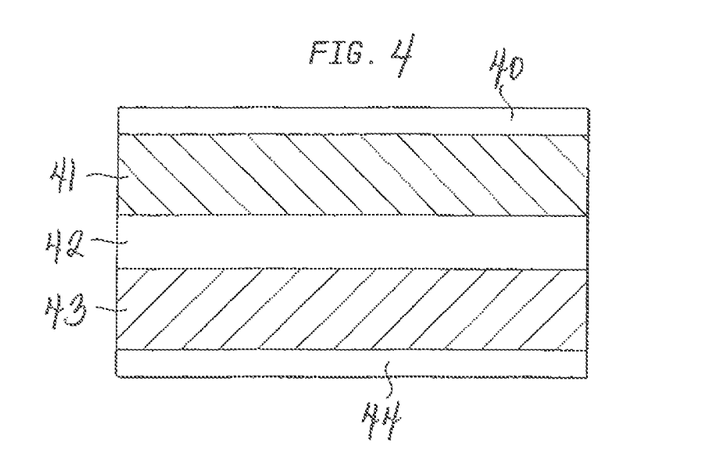
FIG. 4 is a schematic of a 5-layer transdermal delivery device made in accordance with the present invention.

Transdermal delivery devices manufactured according to the present invention may further comprise a membrane layer. Typically, a membrane layer 42, if included, is located between a skin-contact layer 41 and the adhesive layer 43 (the skin-contact layer being adjacent to the release liner 40 and the adhesive layer being adjacent to the backing layer 44). Those skilled in the art will recognize that the skin-contact layer and membrane layer are made, at least partially, of adhesive and should not be confused with adhesive layer 31 or 43.

The membrane layer 42 may serve a variety of purposes, such as controlling diffusion and providing controlled release of the API(s). The membrane layer is selected such that it is rate controlling, i.e., the presence of the membrane layer in the device may change the skin penetration profile of the device compared to a like device not having the membrane.

Suitable membranes include continuous film membranes and microporous membranes. The membrane is preferably made of a flexible, polymeric material used conventionally by those skilled in the art. Polymer films which may be used for making the membrane layer include, without limitation, those comprising low density polyethylene, high density polyethylene, ethylene vinyl acetate copolymers, polypropylene and other suitable polymers.

The membrane thickness can generally range from about 0.25 mil to about 4 mil, preferably, the thickness can range from about 0.7 mil to about 1.3 mil.

One skilled in the art would be able to select an appropriate membrane layer by varying its size, shape, thickness, position relative to the skin, material, porosity, etc. to provide optimal delivery rates of the API to the skin.

The skin-contact layer adjacent to the membrane layer comprises an adhesive. The adhesive may be selected from silicones, natural and synthetic rubbers, polyisobutylene ("PIB") (HMW PIB, LMW PIB, or mixtures of HMW and LMW PIB), neoprenes, polybutadienes, polyisoprenes, polysiloxanes, acrylic adhesives including cross-linked and uncross-linked acrylic copolymers, vinyl acetate adhesives, polyacrylates, ethylene vinyl acetate copolymers, styrene-isoprene copolymers, polyurethanes, plasticized polyether block amide copolymers, plasticized styrene-rubber block copolymers, and mixtures thereof.

In some embodiments, the skin-contact layer contains a mixture of HMW PIB and LMW PIB. In other embodiments, the skin-contact layer contains an API, where the concentration of API in this layer is, preferably, the same as the concentration used in the adhesive layer. In yet other embodiments, the skin-contact layer contains one or more additives, as defined above.

When making a five-layered device, as in FIG. 4, the release liner, skin-contact layer, and membrane layer are fed together as one group. The adhesive layer is then applied to this grouping, followed by addition of an appropriate backing layer. Of course, patches having 4 layers or more than 5 layers may be made by this process.

Although the process can be used for any sized patch, the process of the present invention is particularly suited for use in patches having a surface area larger than about 50 cm$^2$, and preferably ranging from between about 75 cm$^2$ and about 300 cm$^2$.

Without wishing to be bound by any particular theory, it is believed that solvent cast PIB coating processes are typically limited to an 80 or 100 g/m$^2$ coating thickness, while the process according to the present invention is capable of coatings in excess of 1000 g/m$^2$.

Moreover, the patches are suited for patches having any thickness, e.g., patches having adhesive coatings that are about 1 mil or greater in thickness, preferably ranging from between about 5 mil to about 50 mil in thickness. In some embodiments, the patches have a thickness of 10 mils.

Furthermore, the present invention allows for the processing of high viscosity adhesive layers or those containing thermally labile and/or highly volatile APIs.

The process also allows for fine tuning or adjustment of the delivery rates of the API by varying the mechanics of the process used to make the adhesive layer or the properties/arrangements of the layers in the resulting device. For example, one skilled in the art will be able to vary drug loading in the adhesive layer, the thickness of the adhesive layer, the inclusion of additional layers, such as membrane layers, so as to provide optimal API delivery rates. Moreover, one skilled in the art could manipulate parameters of the extrusion process including the size and shape of the augers/screws used, the speed of extrusion, and temperatures utilized during processing to make adhesive layers having different properties.

EXAMPLE

A 27 mm Leistritz brand twin screw extruder ("TSE") was used in this example (a ten zone unit with a screw length-to-diameter ratio (L/D) of 40). The ten zones were configured with top feed inputs on zone 1 and zone 3 and a side-feed on zone 6. The temperature profile in the machine was set with zone 1 at 330° F. and zone 10 at 160° F., with the other zones following that trend. The die was heated to 250° F., with the other down stream temperatures (adapter from extruder to gear pump, gear pump, and adapter from gear pump to die) allowed to follow the temperature of the melt, with a minimum of 160° F.

Zone 1 was fed Oppanol® B-100 (number average molecular weight of about 250,000) from a Bonnot 2" Horizontal single screw extruder, using an oversized auger to compress the B-100 into the single screw extruder. The Bonnot was heated with hot water to 250° F. and its screw speed was set to provide an output of 6.3 kg/hr output. At this point and through zone 2, the TSE screw was designed to provide a minimal amount of shear, but to convey the B-100 quickly downstream.

Zone 3 was fed Oppanol® B-12 (about 51,000 number average molecular weight) and it was processed by two pieces of equipment in series. First, a drum-unloader with a piston-style pump that was electrically heated to 250° F., provided a constant output of B-12 from steel drums. A heated Teflon lined hose connected the drum pump to an electrically heated gear pump, also at 250° F. The gear pump's speed was calibrated to provide an output of 5.1 kg/hr. A thin diameter pipe was used to connect the gear pump to the TSE. At this stage in the TSE, the screw was configured to provide a high degree of shear and mixing. This was to both decrease the domain size of B-100 and to disperse it throughout the B-12, allowing the two polymers to become one polymer with a poly-disperse molecular weight. This shearing and mixing was done through zones 4-5, with a melt seal provided in zone 6.

In zone 6, a K-Tron T-20 refilling a K-Tron T-12 Gravimetric feeder calibrated to feed 0.6 kg/hr, was used to gravimetrically feed Lidocaine <USP> into an awaiting side-stuffer. The side-stuffer, cooled to prevent the API from melting prior to entering the extruder (~90° F.), used twin screws to convey the API into the TSE. The TSE screw flights were very open to allow easy powder induction.

The 7th-9th zones the TSE were used to mix the adhesives and the API into a uniform melt blend. The last zone in the extruder used low pitch screw flights to build pressure prior to the melt entering the gear pump. This increased pressure helped ensure that the gear pump was providing a full amount of material per revolution. The gear pump in turn filled a coat hanger die. At that point, 12 kg/hr of adhesive and API (5% Lidocaine by weight) were shaped into a sheet. The die was set to coat at ~265 mm wide, using the adjustable die lips to ensure a uniform thickness left to right across the die. A coating weight of 200 grams per square meter was targeted. The final adhesive composition comprised about 95% PIB (about 65% Oppanol® B100 and about 35% Oppanol® B-12) and about 5% lidocaine.

The release liner, MediRelease® 2249 was used as a coating substrate, with the hot melt layering onto it. The backing layer, Mediflex 1501® (Mylan), was laminated on top of the extrudate. This multilayer laminate passed through chilled calendaring rolls held at 105° F. and continued through a 3-roll S-wrap, further cooling the laminate.

The chilled rolls were wound onto 3" diameter cores. The wound laminates were then slit, trimming edge waste, from both the extrudate and the incoming backing and skin contact layer, which were oversized up to this point. The slitting also proportioned the cuts to allow for slightly oversized material to be die cut. A rotary die was then used to make the appropriate sized finished systems, prior to pouching.

Additional Examples

The invention can also be used to produce placebo material by removing or disabling the side stuffing API feeder and adjusting the PIB feed rates to compensate for the lack of API. With these modifications, placebo material was fed into the die and shaped into a sheet between the backing and release liner as previously described. Prototypes were produced at 200 and 1000 g/m$^2$ coating thickness at 65/35 and 45/55 B-100 to B-12, respectively demonstrating that a wide range of thickness and PIB ratio can be produced.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A continuous process for the production of an adhesive composition comprising:
   a) pre-processing a non-granulated high molecular weight polyisobutylene (HMW PIB) having a molecular weight ranging from about 200,000 g/mol to about 425,000 g/mol in a single-screw extruder to form a bulk HMW PIB material, wherein said bulk HMW PIB material is in a compressed, continuous feed form;
   b) extruding said bulk HMW PIB material in an extruding apparatus, wherein said HMW PIB is extruded;
   c) simultaneously extruding said extruded HMW PIB with low molecular weight polyisobutylene (LMW PIB) in said extruding apparatus to produce high shear so as to form an extruded melt, wherein a ratio of the amount of HMW PIB to LMW PIB in said melt is about 65:35;
   d) adding an active pharmaceutical ingredient (API) to said extruded melt to produce an extruded API/PIB melt; and
   e) discharging said extruded API/PIB melt to a die to form said adhesive composition, wherein said adhesive composition comprises about 93% to about 97% PIB and about 3% to about 7% API.

2. The process of claim 1, wherein said single screw extruder is heated to a temperature between about 85° F. and about 500° F.

3. The process of claim 1, wherein said high molecular weight polyisobutylene has a molecular weight ranging from about 250,000 g/mol to about 425,000 g/mol.

4. The process of claim 1, wherein said HMW PIB and said LMW PIB are simultaneously extruded in a twin-screw extruder.

5. The process of claim 1, wherein said low molecular weight polyisobutylene has a molecular weight ranging from about 35,000 g/mol to about 100,000 g/mol.

6. The process of claim 1, wherein said low molecular weight polyisobutylene has a molecular weight ranging from about 36,000 g/mol to about 75,000 g/mol.

7. The process of claim 1, wherein said low molecular weight polyisobutylene is heated to a temperature between about 65° F. and about 500° F.

8. The process of claim 1, wherein said active pharmaceutical ingredient is selected from the group consisting of an opioid receptor antagonist, anesthetics, local anesthetics, anti-asthmatics, anti-inflammatory substances, opiates, bronchodilators, analgesics, anti-hypertensive drugs, hormones, contraceptives, anti-nauseants, anti-histamines, stimulants, anti-anginal drugs, opiate receptor agonists, dopamine agonists, anticholinergics, neuromuscular drugs, anabolic drugs, anti-emetics, decongestants, vasoconstrictors, sedatives, psychotropics, diuretics, vasodilators, hypnotics, anti-pyretics, and anti-spasmodics.

9. The process of claim 1, wherein said active pharmaceutical ingredient is selected from the group consisting of lidocaine, piroxicam, fentanyl, sufentanyl, albuterol, buprenorphine, clonidine, diclofenac, estradiol, ethinyl estradiol, granisetron, ketoprofen, loratadine, memantine, methylphenidate, naltrexone, nicotine, nitroglycerin, norelgestromin, oxybutynin, risperidone, rivastigmine, rotigotine, scopolamine, selegiline, testosterone, desloratadine, dexmethylphenidate, and tulobuterol.

10. The process of claim 1, further comprising adding one or more additives to said API/PIB melt.

11. The process of claim 1, further comprising laminating said adhesive composition between a backing layer and a release liner to produce a transdermal delivery device.

12. A continuous process for the production of an adhesive composition comprising:
a) pre-processing a non-granulated high molecular weight polyisobutylene (HMW PIB) having a molecular weight ranging from about 200,000 g/mol to about 425,000 g/mol in a single-screw extruder to form a bulk HMW PIB material, wherein said bulk HMW PIB material is in a compressed, continuous feed form;
b) extruding said bulk HMW PIB material having a molecular weight ranging from about 200,000 g/mol to about 425,000 g/mol in a twin-screw extruding apparatus, wherein said HMW PIB is extruded;
c) simultaneously extruding said extruded HMW PIB with low molecular weight polyisobutylene (LMW PIB) in said extruding apparatus to produce high shear so as to form an extruded melt; wherein said LMW PIB has a molecular weight ranging from about 35,000 g/mol to about 100,000 g/mol; and wherein a ratio of the amount of HMW PIB to LMW PIB in said melt is about 65:35;
d) adding an active pharmaceutical ingredient to said extruded melt to produce an extruded API/PIB melt; and
e) discharging said extruded API/PIB melt to a die to form said adhesive composition, wherein said adhesive composition comprises about 93% to about 97% PIB and about 3% to about 7% API.

13. The process of claim 12, wherein said HMW PIB has a number average molecular weight of about 250,000, said LMW PIB has a number average molecular weight of about 51,000 and said API is lidocaine.

14. The process of claim 1, wherein the HMW PIB is free from fillers.

15. The process of claim 1, wherein the API is lidocaine, and said adhesive composition comprises lidocaine in an amount of about 5%.

* * * * *